United States Patent
Jang et al.

(10) Patent No.: US 10,760,174 B2
(45) Date of Patent: Sep. 1, 2020

(54) LEVELING AGENT AND ELECTROPLATING COMPOSITION COMPRISING THE SAME

(71) Applicant: SOULBRAIN CO., LTD., Seongnam-si, Gyeonggi-do (KR)

(72) Inventors: Min Jung Jang, Seongnam-si (KR); Jong Cheol Yun, Seongnam-si (KR); Wan Joong Kim, Seongnam-si (KR); Hee Jeong Ryu, Seongnam-si (KR); Seung Min Park, Seongnam-si (KR)

(*) Notice: Subject to any disclaimer, the term of this patent is extended or adjusted under 35 U.S.C. 154(b) by 0 days.

(21) Appl. No.: 16/191,464

(22) Filed: Nov. 15, 2018

(65) Prior Publication Data
US 2019/0161878 A1  May 30, 2019

(30) Foreign Application Priority Data
Nov. 28, 2017  (KR) .................. 10-2017-0160202

(51) Int. Cl.
| | | |
|---|---|---|
| C25D 3/38 | (2006.01) |
| H01L 21/768 | (2006.01) |
| H01L 21/288 | (2006.01) |
| C07D 275/03 | (2006.01) |
| C07D 275/04 | (2006.01) |
| C25D 7/12 | (2006.01) |

(52) U.S. Cl.
CPC .............. *C25D 3/38* (2013.01); *C07D 275/03* (2013.01); *C07D 275/04* (2013.01); *H01L 21/2885* (2013.01); *H01L 21/76879* (2013.01); *C25D 7/123* (2013.01)

(58) Field of Classification Search
None
See application file for complete search history.

(56) References Cited

FOREIGN PATENT DOCUMENTS

| CN | 101955709 | * | 1/2011 |
| CN | 103965669 | * | 8/2014 |
| KR | 1020040045328 A | | 6/2004 |

* cited by examiner

*Primary Examiner* — Kamal A Saeed
(74) *Attorney, Agent, or Firm* — Jongkook Park

(57) ABSTRACT

The present invention relates to a leveling agent and electroplating composition comprising the same. When features are plated using the electroplating composition of the present invention, excellently leveled plated surfaces with minimized defects may be obtained.

8 Claims, No Drawings

LEVELING AGENT AND ELECTROPLATING COMPOSITION COMPRISING THE SAME

CROSS-REFERENCE TO RELATED APPLICATIONS

This application claims priority under 35 U.S.C. § 119 to Korean patent application no. 10-2017-0160202 filed on Nov. 28, 2017, in the Korean intellectual property office, the disclosure of which is incorporated herein by reference in its entirety.

FIELD OF THE INVENTION

The present invention relates to an electroplating composition used for electroplating and a leveling agent included therein.

BACKGROUND OF THE INVENTION

As interconnections become multilayered upon the manufacture of a semiconductor device, features with high aspect ratios, e.g., vias or trenches, are formed on a substrate. The features are charged by electroplating a composition. At this time, to minimize defects such as voids and seams, additives such as accelerators, suppressors, or leveling agents may be included in the electroplating composition.

During the process of electroplating using an electroplating composition containing accelerator, bumps are formed due to the presence of the accelerator. As the plating process proceeds, an aggregation of bumps is formed as the bumps grow. At such a time, due to the accelerated formation of the bumps on regions with high aspect ratios and high density, like the features, a bigger aggregation is formed. Such a phenomenon is called overplating. The areas where overplating has occurred form steps from the surrounding regions, and the formed steps cause defects in semiconductor devices due to increase of the processing time during the chemical mechanical polishing process and impedance of surface smoothness.

Accordingly, a leveling agent is added to increase the smoothness of the surface. Conventionally, the use of polyethyleneimine, polyglycine, polyurea, polyacrylamide, polyaminoamide, polyalkanolamine, and so forth as leveling agents has been disclosed. In addition, the use of copolymers of polyvinylpyridine, polyvinylpyrrolidone, vinylimidazole, vinylpyrrolidone, and so on as leveling agents has also been disclosed.

However, such leveling agents still have limits to increase surface smoothness. Accordingly, there is a demand for copper electroplating additives, and which can further improve the smoothness of plated surfaces.

Patent Literature: KR 2004-0045328

SUMMARY OF THE INVENTION

It is an object of the present invention to provide a leveling agent capable of improving the leveling of a plated surface to solve the aforementioned problems.

It is another object of the present invention to provide an electroplating composition including the leveling agent.

It is an object of the present invention to provide a leveling agent comprising a compound expressed in the chemical formula below, to solve the aforementioned problems.

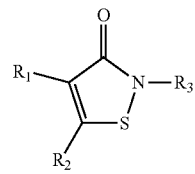

[Chemical Formula 1]

In Chemical Formula 1,
$R_1$ and $R_2$ are groups which are the same as or different from each other, each of which is independently selected from a group of hydrogen, halogens, and $C_1$ to $C_{10}$ alkyls, and which may also form a fused ring by being combined with each other; and $R_3$ is a group selected from among a hydrogen or $C_1$ to $C_{10}$ alykl group In addition, the present invention provides an electroplating composition, comprising: a metal ion supply source; electrolyte; and a leveling agent.

DETAILED DESCRIPTION OF THE PREFERRED EMBODIMENTS

The present invention is explained below in detail.
1. Leveling Agent
A leveling agent of the present invention may include a compound expressed by Chemical Formula 1 below.

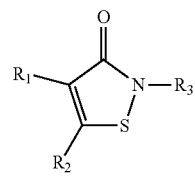

[Chemical Formula 1]

In Chemical Formula 1, $R_1$ and $R_2$ are groups which may be the same as or different from each other, each of which is independently selected from a group of hydrogen, halogens, and $C_1$ to $C_{10}$ alkyl groups, and which may form a fused ring by being combined with each other, while $R_3$ is a group selected from among hydrogen or a $C_1$ to $C_{10}$ alkyl group.

A compound expressed by Chemical Formula 1 is an isothiazolinone compound. When features formed on a substrate are electroplated using an electroplating composition including the leveling agent, the compound may plate (or charge) the features while achieving a state of minimized defects such as voids, seams, and the like, by facilitating strong adherence to a metal surface. In addition, as it suppresses the growth of metal on a substrate surface other than the features, the leveling of the surface is increased, allowing an evenly plated substrate to be obtained.

Herein, in consideration of the characteristics of the leveling agent, e.g., leveling, it is desirable that $R_1$ and $R_2$ in the compound expressed by Chemical Formula 1 are the same as or different from each other, and that each of them is a hydrogen or halogen, independently. Specifically, it is more desirable that $R_1$ is hydrogen and $R_2$ is chlorine (Cl).

Moreover, given the characteristics of the leveling agent, it is desirable that $R_3$ in the compound expressed by Chemical Formula 1 is hydrogen. A compound expressed by Chemical Formula 1 may be specified as one of the compounds selected from the group of compounds expressed in Chemical Formulas 2 to 4 as shown below, but it is not limited thereto.

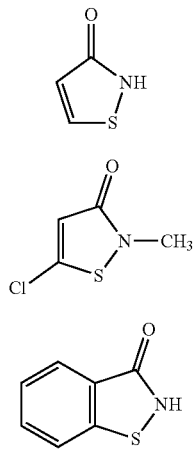

[Chemical Formula 2]

[Chemical Formula 3]

[Chemical Formula 4]

2. Electroplating Composition

An electroplating composition of the present invention may include a metal ion supply source, an electrolyte, and a leveling agent.

The metal ion supply source supplies metal ions during a plating process. Selection of such a metal ion supply source is not limited, but it is desirable to use a copper salt. For example, the copper salt can be copper sulfate, copper chloride, copper acetate, copper citrate, copper nitrate, copper fluoroborate, copper methane sulfonate, copper phenyl sulfonate, copper p-toluene sulfonate, or mixtures thereof.

The content of the metal ion supply source is not specifically limited, but in consideration of electroplating efficiency, it is desirable that the content be 15-25 wt % based on the total weight of the metal ion supply source, the electrolyte, and the leveling agent. If the content of the metal ion supply source is less than 15 wt % or exceeds 25 wt %, the metal ion may not be provided smoothly or may be overprovided, resulting in the formation of defects such as voids or seams.

The electrolyte gives conductivity to an electroplating composition. It is desirable that the electrolyte is acidic, and as a more specific example, sulfuric acid, acetic acid, fluoroboric acid, methane sulfonic acid, ethanesulfonic acid, propanesulfonic acid, trifluoromethanesulfonic acid, benzenesulfonic acid, p-toluenesulfonic acid, sulfamic acid, hydrochloric acid, hydrobromic acid, perchloric acid, nitric acid, chromic acid, phosphoric acid, or mixtures thereof may be employed.

The content of the electrolyte is not specifically limited, but in consideration of electroplating efficiency, it is desirable that the content be 0.001-10 wt % based on the total weight of the metal ion supply source, the electrolyte, and the leveling agent. If the content of the electrolyte is less than 0.001 wt % or exceeds 10 wt %, a local electroplating phenomenon could occur or the quality of a layer could be deteriorated, thereby inducing defects to occur in the electroplating layer during the course of annealing.

The leveling agent controls the leveling of an electroplated surface during the course of electroplating. Explanation of the leveling agent is omitted here because it is the same as what has been explained in '1. Leveling agent' as described above.

The content of the leveling agent is not specifically limited, but in consideration of electroplating efficiency and the leveling of the electroplated surface, it is desirable that the content be 0.0001 to 0.02 wt % based on the total weight of the metal ion supply source, the electrolyte, and the leveling agent. If the content of the leveling agent is less than 0.0001 wt %, defects such as voids may occur because plating on the upper part of a pattern cannot be suppressed, and even if bottom-up occurs, bumps can conventionally be formed at a higher level due to the accumulated concentration of an accelerator. If the content of the leveling agent exceeds 0.02 wt %, excessive suppression might prevent plating from being properly formed on an electroplated layer, and dimples can be formed even if bottom-up occurs.

Meanwhile, an electroplating composition of the present invention may further include an accelerator and a suppressor to increase electroplating efficiency. The accelerator increases the plating speed of the metal ions during the electroplating process. Such an accelerator is not limited here, but some specific examples may include N, N-dimethyl-dithiocarbamic acid-(3-sulfopropyl) ester, 3-mercapto-propylsulfonic acid-(3-sulfopropyl) ester, 3-mercapto-propylsulfonic acid sodium salt, bis-sulfopropyl-disulfide, bis-(sodium sulfopropyl)-disulfide, 3-(benzothiazolyl-s-thio) propylsulfonic acid sodium salt, pyridinium propyl sulfobetaine, 1-sodium-3-mercaptopropane-1-sulfonate, N, N-dimethyl-dithiocarbamic acid-(3-sulfoethyl) ester, 3-mercapto-ethylprophyl sulfonic acid-(3-sulfoethyl) ester, 3-mercapto-ethylsulfonic acid sodium salt, bis-sulfoethyl disulfide, 3-(benzothiazolyl-s-thio) ethylsulfonic acid sodium salt, pyridinium ethyl sulfobetaine, 1-sodium-3-mercaptoethane-1-sulfonate, or mixtures thereof.

The content of the accelerator is not limited here, but in consideration of electroplating efficiency, it is desirable that it would be from 0.0001 to 0.02% by weight based on the gross weight of the copper plating composition. If the content of the accelerator is less than 0.0001% by weight, gloss of the plating surface may be reduced, and if the content of the accelerator exceeds 0.02% by weight, defects could occur due to initial excessive plating, or adhesion may become weak.

The suppressor suppresses the reduction speed of metal ions during the electroplating process, thereby controlling the speed of plating of the metal ions. Such a suppressor is not limited here, but specific examples may include Polyethylene Glycol, Polypropylene Glycol, Polyethylene Glycol monoamine, Polypropylene Glycol monoamine, Polyethylene Glycol diamine, Polypropylene Glycol diamine, Polyethylene Glycol monothiol, Polypropylene Glycol monothiol, Polyethylene Glycol dithiol, Polypropylene Glycol dithiol, Polyethylene Glycol monoalkylether, Polypropylene Glycol monoalkylether, Polyethylene Glycol dialkylether, Polypropylene Glycol dialkylether, or a copolymer of Ethylene Oxide and Propylene Oxide and the like.

The content of the suppressor is not limited here, but in consideration of electroplating efficiency, it is desirable that it would be from 0.0001 to 1% by weight based on the gross weight of the copper plating composition. If the content of the suppressor is less than 0.0001% by weight, the uniformity of the plating may not be good, and if the content of the suppressor exceeds 1% by weight, the plating speed could be reduced.

Moreover, the electroplating composition of the present invention may further include an additional solvent, which may be water.

The electroplating composition of the present invention may further optionally include additives such as a surfactant, an antifoaming agent, or a pH regulator, as known in the related art.

Because the electroplating composition of the present invention includes the leveling agent explained above, when electroplating is performed using the composition, a plated surface with excellent leveling may be obtained. In particular, the electroplating composition of the present invention may display more excellent leveling when electroplating is performed on features for which the size of the feature gaps formed on the substrate is 5-50 um and the aspect ratio of the features is 1:3-1:10.

A detailed explanation of the present invention is provided through examples, as shown below. However, these examples are only illustrative examples, and thus the present invention is not limited thereto.

EXAMPLES 1-3

Individual electroplating compositions were prepared with the components shown in Table 1, as follows:

TABLE 1

| Components | | Example 1 | Example 2 | Example 3 |
|---|---|---|---|---|
| | | | | (Unit: wt %) |
| Metal Ion Supply Source | Copper Sulfate | 17 | 17 | 17 |
| Electrolytes | Sulfuric Acid | 5 | 5 | 5 |
| | Hydrochloric Acid | 0.005 | 0.005 | 0.005 |
| Leveling Agents | [structure] | 0.001 | — | — |
| | [structure] | — | 0.002 | — |
| | [structure] | — | — | 0.001 |
| Accelerator | bis(3-sulfopropyl disulfide) (SPS) | 0.002 | 0.002 | 0.002 |
| Suppressor | PEG-PPG | 0.02 | 0.02 | 0.02 |
| Solvent | Water (DI water) | Remaining Amount | Remaining Amount | Remaining Amount |
| | TOTAL | 100 | 100 | 100 |

COMPARATIVE EXAMPLES 1-2

Individual electroplating compositions were prepared with the components shown in Table 2, as follows:

TABLE 2

| Ingredients | | Comparative Example 1 | Comparative Example 2 |
|---|---|---|---|
| Metal Ion Supply Source | Copper Sulfate | 17 | 17 |
| Electrolytes | Sulfuric Acid | 5 | 5 |
| | Hydrochloric Acid | 0.005 | 0.05 |
| Leveling Agents | [structure] | 0.001 | — |
| | [structure] | — | 0.001 |
| Accelerator | bis(3-sulfopropyl disulfide (SPS) | 0.002 | 0.002 |
| Suppressor | PEG-PPG | 0.02 | 0.02 |
| Solvent | Water (DI water) | Remaining Amount | Remaining Amount |
| | TOTAL (wt %) | 100 | 100 |

EXPERIMENTAL EXAMPLE

Patterned wafers with a size of 5 um and an aspect ratio of 1:10 were inserted into electroplating baths filled with electroplating compositions prepared according to each of the examples and the comparative examples, respectively, and electroplating was conduct for 1 ASD at 1000 rpm for 25 minutes.

After completion of the electroplating, the leveling of the patterned wafers was evaluated. Here, the inside of a hole (pattern) was represented as H1 and the outside thereof as a bulk area, H2. The ratios of H1/H2 are represented in Table 3 below. (A ratio close to 1 indicates smoother leveling of the surface.)

TABLE 3

| | Example 1 | Example 2 | Example 1 | Comparative Example 1 | Comparative Example 2 |
|---|---|---|---|---|---|
| Leveling (H1/H2) | 1.10 | 0.97 | 0.91 | 0.72 | 0.65 |

Referring to Table 3, it can be confirmed that when electroplating is conducted with the electroplating compositions prepared in accordance with examples 1 to 3, uniform and excellently leveled electroplated surfaces are obtained. In contrast, it can be observed that when electroplating is conducted with electroplating compositions prepared in accordance with the comparative examples 1 and 2, the resulting electroplated surfaces were uneven and had occurrence of defects.

Since the electroplating composition of the present invention includes the compound expressed by Chemical Formula 1 as a leveling agent, when electroplating is performed by using the composition, an evenly leveled plated surface may be obtained. Accordingly, the present invention may allow even plating of a substrate with minimized defects, which may improve the confidence of consumers of semiconductor devices.

What is claimed is:

1. A leveling agent for electroplating comprising a compound of Chemical Formula 1, as follows:

[Chemical Formula 1]

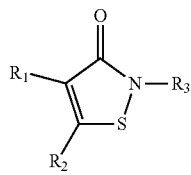

In Chemical Formula 1, $R_1$ and $R_2$ are groups which are the same as or different from each other, each of which is independently selected from a group of hydrogen, halogens, and $C_1$ to $C_{10}$ alkyls, and which may form a fused ring by being combined with each other; and $R_3$ is a group selected from hydrogen and $C_1$ to $C_{10}$ alkyls.

2. The leveling agent for electroplating of claim 1, wherein $R_1$ and $R_2$ are hydrogen or halogens.

3. The leveling agent for electroplating of claim 2, wherein the halogen is chlorine (Cl).

4. The leveling agent for electroplating of claim 1, wherein $R_3$ is hydrogen.

5. The leveling agent for electroplating of claim 1, wherein the compound expressed by Chemical formula 1 is a group selected from the compounds of the following Chemical Formulas 2 to 4:

[Chemical Formula 2]

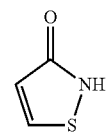

[Chemical Formula 3]

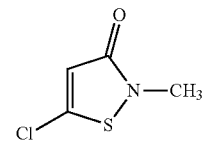

[Chemical Formula 4]

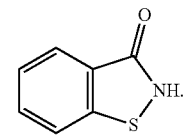

6. An electroplating composition, comprising:
   A metal ion supply source;
   An electrolyte; and
   a leveling agent described in claim 1.

7. The electroplating composition of claim 6, wherein the content of the leveling agent is 0.0001 to 0.02 wt % based on the total weight of the metal ion supply source, the electrolyte, and the leveling agent.

8. The electroplating composition of claim 6, further comprising: an accelerator and a suppressor.

* * * * *